United States Patent
Wolters et al.

(10) Patent No.: US 7,773,212 B1
(45) Date of Patent: Aug. 10, 2010

(54) CONTEMPORANEOUS SURFACE AND EDGE INSPECTION

(75) Inventors: Christian Wolters, Campbell, CA (US); Anatoly Romanovsky, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 12/124,778

(22) Filed: May 21, 2008

(51) Int. Cl.
*G01N 21/00* (2006.01)
(52) U.S. Cl. .................................. 356/237.4; 356/237.5
(58) Field of Classification Search ... 356/237.1–237.6, 356/239.1, 239.3, 239.7, 239.8, 600, 337–340, 356/369, 630–640, 429–431, 614–615, 399–400, 356/620–622; 250/234–236, 559.45–559.49, 250/548, 442, 492.2, 202; 414/935–941, 414/757, 222.01–222.02
See application file for complete search history.

(56) References Cited

U.S. PATENT DOCUMENTS

| 6,262,432 | B1 * | 7/2001 | Brunfeld et al. | 250/559.45 |
| 2008/0117415 | A1 * | 5/2008 | Hamamatsu et al. | 356/237.4 |
| 2008/0316505 | A1 * | 12/2008 | Graf et al. | 356/614 |

* cited by examiner

*Primary Examiner*—Gregory J Toatley, Jr.
*Assistant Examiner*—Tri T Ton
(74) *Attorney, Agent, or Firm*—Luedeka, Neely & Graham, P.C.

(57) ABSTRACT

In one embodiment, a surface analyzer system comprises a first radiation source to generate radiation at a first wavelength, a surface inspection assembly, and an edge detection assembly. In operation, the system enables contemporaneous surface inspection and edge detection.

9 Claims, 4 Drawing Sheets

CONTEMPORANEOUS SURFACE AND EDGE INSPECTION

RELATED APPLICATIONS

None

BACKGROUND

The subject matter described herein relates to surface inspection techniques, and more particularly to contemporaneous surface and edge detection and/or inspection.

Semiconductor materials may be inspected for defects such as, e.g., surface imperfections, particles, irregularities in the thickness of thin film coatings, and the like, which may hamper the performance of the semiconductor material. Some existing inspection systems direct a beam of radiation on the surface of the semiconductor material, then collect and analyze light reflected and/or scattered from the surface to quantify characteristics of the surface. Additional inspection techniques are desirable. In particular, it is desirable to inspect the edge or near edge of semiconductor wafers, compound semiconductor wafers, transparent wafers or thin film disks for defects.

BRIEF DESCRIPTION OF THE DRAWINGS

The detailed description is described with reference to the accompanying figures.

DETAILED DESCRIPTION

Figure 1:
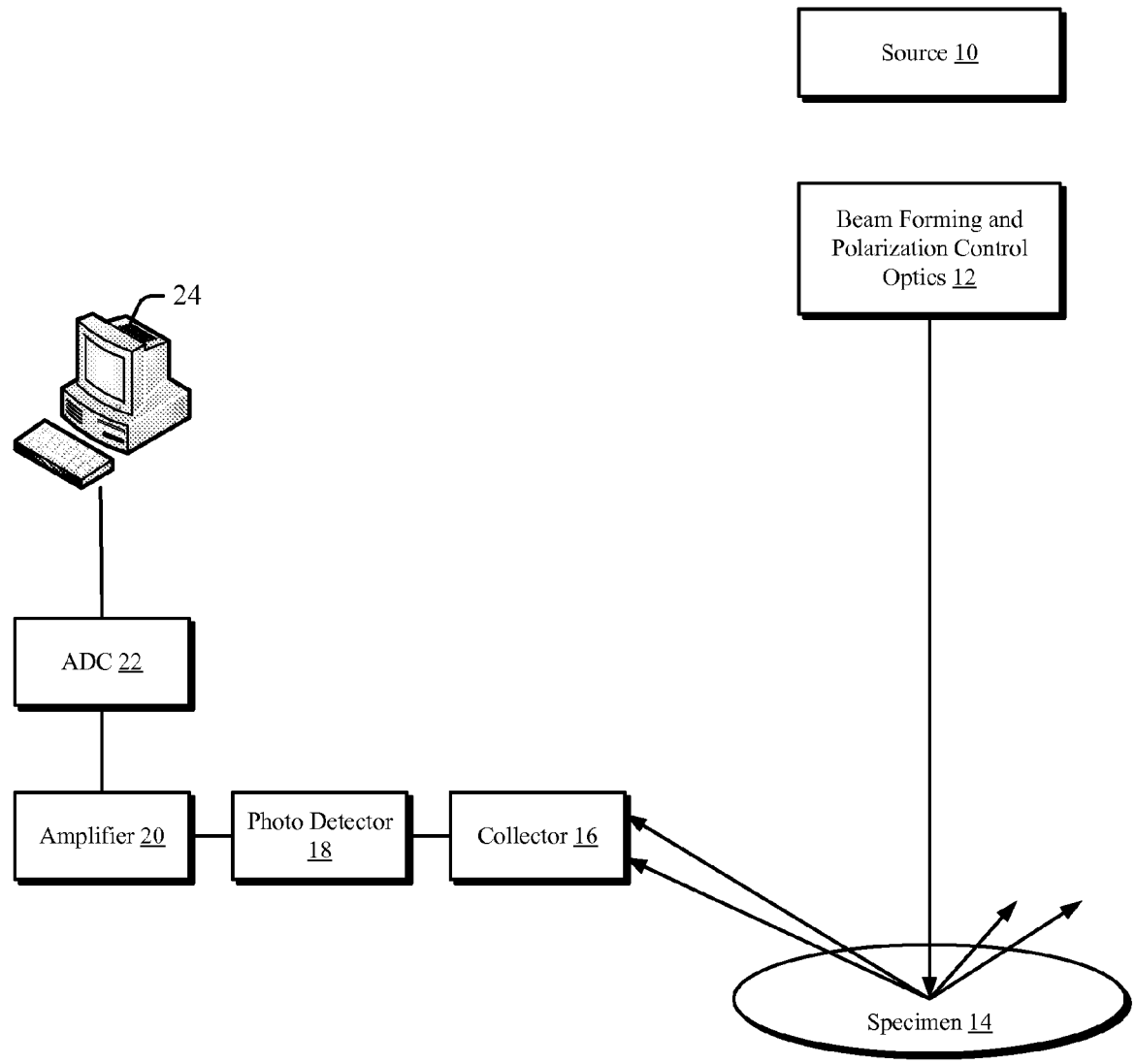
FIG. 1 is a schematic illustration of various components of a surface inspection system, according to embodiments.

Described herein are exemplary systems and methods for contemporaneous surface inspection and edge inspection and/or detection in surface inspection systems. In the following description, numerous specific details are set forth in order to provide a thorough understanding of various embodiments. However, it will be understood by those skilled in the art that the various embodiments may be practiced without the specific details. In other instances, well-known methods, procedures, components, and circuits have not been described in detail so as not to obscure the particular embodiments.

Various methods described herein may be embodied as logic instructions on a computer-readable medium. When executed on a processor the logic instructions cause a processor to be programmed as a special-purpose machine that implements the described methods. The processor, when configured by the logic instructions to execute the methods described herein, constitutes structure for performing the described methods.

Various embodiments are described herein for an optical inspection system or tool that may be used for inspecting a specimen. The term "specimen" is used herein to refer to a wafer, a reticle, or any other sample that may be inspected for defects, features, or other information (e.g., an amount of haze or film properties) known in the art.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

In some cases, a wafer may include only the substrate, such as a virgin wafer. Alternatively, a wafer may include one or more layers that may be formed upon a substrate. Examples of such layers may include, but are not limited to, a resist, a dielectric material, and a conductive material. A resist may include a resist that may be patterned by an optical lithography technique, an e-beam lithography technique, or an X-ray lithography technique. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials, such as "xerogels," and "high-k" dielectric materials, such as tantalum pentoxide. In addition, examples of conductive materials may include, but are not limited to, aluminum, polysilicon, and copper.

One or more layers formed on a wafer may be "patterned" or "unpatterned." For example, a wafer may include a plurality of dies having repeatable pattern features. Formation and processing of such layers of material may ultimately result in completed semiconductor devices. As such, a wafer may include a substrate on which not all layers of a complete semiconductor device have been formed, or a substrate on which all layers of a complete semiconductor device have been formed. The term "semiconductor device" may be used interchangeably herein with the term "integrated circuit." In addition, other devices such as microelectromechanical (MEMS) devices and the like may also be formed on a wafer.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source.

FIG. 1 is a schematic illustration of various components of a surface inspection system, according to embodiments. The system shown in FIG. 1 illustrates a general optical configuration that can be used to inspect a specimen according to the methods described herein. The inspection system includes a dark-field optical subsystem. It will be obvious to one of ordinary skill in the art that the illustrated system may be altered in many ways while still providing the capability to perform the methods described herein. In addition, it will be obvious to one of ordinary skill in the art that the illustrated system may include various additional components that are not shown in FIG. 1 such as a stage, a specimen handler, folding mirrors, polarizers, additional light sources, additional collectors, etc. All such variations are within the scope of the invention described 10 herein.

The system illustrated in FIG. 1 includes an illumination subsystem. The illumination subsystem is configured to direct light to a specimen. For example, the illumination subsystem includes light source 10. Light source 10 may include, for example, a laser, a diode laser, a helium neon laser, an argon laser, a solid state laser, a diode pumped solid state (DPSS) laser, a xenon arc lamp, a gas discharging lamp, or an incandescent lamp. The light source may be configured to emit near monochromatic light or broadband light. In general, the illumination subsystem is configured to direct light having a relatively narrow wavelength band to the specimen (e.g., nearly monochromatic light or light having a wavelength range of less than about 20 nm, less than about 10 nm, less than about 5 nm, or even less than about 2 nm). Therefore, if the light source is a broadband light source, the illumination subsystem may also include one or more spectral filters that may limit the wavelength of the light directed to the specimen. The one or more spectral filters may be bandpass filters and/or edge filters and/or notch filters.

The illumination subsystem also includes various beam forming and polarization control optics 12. For example, the illumination subsystem may include various optics for directing and supplying an incident beam to specimen 14 with, e.g., a particular spot size. If the light source is configured to emit light of various polarizations, the illumination subsystem may also include one or more polarizing components that may alter the polarization characteristics of the light emitted by the light source. In some cases, the light directed to specimen 14 may be coherent or incoherent. The beam forming and polarization control optics 12 may include a number of components, which are not shown in FIG. 1, such as a beam expander, folding mirrors, focusing lenses, cylindrical lenses, beam splitters, etc.

In some cases, the illumination subsystem may include a deflector (not shown). In one embodiment, the deflector may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector scans the light beam over the specimen. In some embodiments, the deflector may scan the light beam over the specimen at an approximately constant scanning speed.

As shown in FIG. 1, the illumination subsystem may be configured to direct the beam of light to the specimen at a normal angle of incidence. In this embodiment, the illumination subsystem may not include a deflector since the normal incidence beam of light may be scanned over the specimen by relative motion of the optics with respect to the specimen and/or by relative motion of the specimen with respect to the optics. Alternatively, the illumination subsystem may be configured to direct the beam of light to the specimen at an oblique angle of incidence. The system may also be configured to direct multiple beams of light to the specimen such as an oblique incidence beam of light and a normal incidence beam of light. The multiple beams of light may be directed to the specimen substantially simultaneously or sequentially.

The inspection system of FIG. 1 includes a single collection channel. For example, light scattered from the specimen may be collected by collector 16, which may be a lens, a compound lens, or any appropriate lens known in the art. Alternatively, collector 16 may be a reflective or partially reflective optical component, such as a mirror. In addition, although one particular collection angle is illustrated in FIG. 1, it is to be understood that the collection channel may be arranged at any appropriate collection angle. The collection angle may vary depending upon, for example, the angle of incidence and/or topographical characteristics of the specimen.

The inspection system also includes a detector 18 for detecting the light scattered from the specimen and collected by collector 16. Detector 18 generally functions to convert the scattered light into an electrical signal, and therefore, may include substantially any photodetector known in the art. However, a particular detector may be selected for use within one or more embodiments of the invention based on desired performance characteristics of the detector, the type of specimen to be inspected and/or the configuration of the illumination subsystem. For example, if the amount of light available for inspection is relatively low, an efficiency enhancing detector such as a time delay integration (TDI) camera may increase the signal-to-noise ratio and throughput of the system. However, other detectors such as charge-coupled device (CCD) cameras, photodiodes, phototubes and photomultiplier tubes (PMTs) may be used, depending on the amount of light available for inspection and the type of inspection being performed. In at least one embodiment of the invention, a photomultiplier tube is used for detecting light scattered from a specimen.

The inspection system also includes various electronic components needed for processing the scattered signals detected by detector 18. For example, the system shown in FIG. 1 includes amplifier circuitry 20, analog-to-digital converter (ADC) 22 and processor 24. Amplifier 20 is generally configured to receive output signals from detector 18 and to amplify those output signals by a predetermined amount. ADC 22 converts the amplified signals into a digital format suitable for use within processor 24. In one embodiment, the processor may be coupled directly to ADC 22 by a transmission medium, as shown in FIG. 1. Alternatively, the processor may receive signals from other electronic components coupled to ADC 22. In this manner, the processor may be indirectly coupled to ADC 22 by a transmission medium and any intervening electronic components.

In general, processor 24 is configured for detecting features, defects, or light scattering properties of the specimen using electrical signals obtained from the single collection channel. The signals produced by the single collection channel are representative of the light detected by a single detector (detector 18). The term "single detector" may be used herein to describe a detector having only one sensing area, or possibly several sensing areas (such as found, e.g., in a detector array or multi-anode PMT). Regardless of number, the sensing areas of a single detector are embodied within a single enclosure. In some cases, the inspection system described herein may be used for inspecting patterned, as well as unpatterned specimens. The processor may include any appropriate processor known in the art. In addition, the processor may be configured to use any appropriate defect detection algorithm or method known in the art. For example, the processor may use a die-to-database comparison or a thresholding algorithm to detect defects on the specimen.

Additional embodiments of inspection systems in which the subject matter described herein may find utility are described in U.S. Pat. Nos. 6,538,730, 6,271,916, 6,201,601, 6,956,660, 7,218,391, and 7,061,601, the disclosures of which are incorporated herein by reference in their entirety. These inspections systems generally operate by mounting an object on a rotatable spindle assembly, which in turn comprises a chuck on which the object may be mounted. A first drive assembly rotates the spindle about a central axis, such that the first radiation beam and the second radiation beam scan a portion of the surface of the object, while a second drive assembly induces radial motion between the optical assembly and the object being inspected, such that a radiation beam is scanned across the surface of the object. In alternate embodiments, an inspection system may implement an X-Y scanning pattern to scan the surface of the object.

In some embodiments, the inspection system may be adapted to provide a system and method to permit contemporaneous inspection of the surface of an object such as, e.g., a wafer, and the detection of, alone or in combination with the inspection of, an edge of the wafer.

In some embodiments the system comprises a first radiation source to generate radiation at a first wavelength, a surface inspection assembly, and an edge detection assembly. The surface inspection assembly comprises a first radiation targeting assembly to scan a first radiation beam from the first radiation source across a portion of a first surface of the object, a first scattered radiation collecting assembly to collect portions of a first scattered radiation beam scattered from the first surface, wherein the first scattered radiation beam results from a reflection of the first radiation beam, and a first detector assembly coupled to the scattered radiation collecting assembly to generate a first signal from the first scattered radiation beam.

The edge detection assembly comprises a second radiation targeting assembly to direct a second radiation beam across a portion of an edge surface of the object, a throughbeam detector to generate a third signal set from a portion of the radiation from the second radiation targeting assembly a second scattered radiation collecting assembly to collect portions of a second scattered radiation beam scattered from the edge surface, wherein the first scattered radiation beam results from a reflection of the second radiation beam, and a second detector assembly coupled to the scattered radiation collecting assembly to generate a second signal from the second scattered radiation beam.

In some embodiments, the system further comprises at least one signal processing module to generate a first signal set from the first signal and a second signal set from the second signal, and a data processing module to use data in the data set to evaluate defects in the surface of the object.

Figure 2:
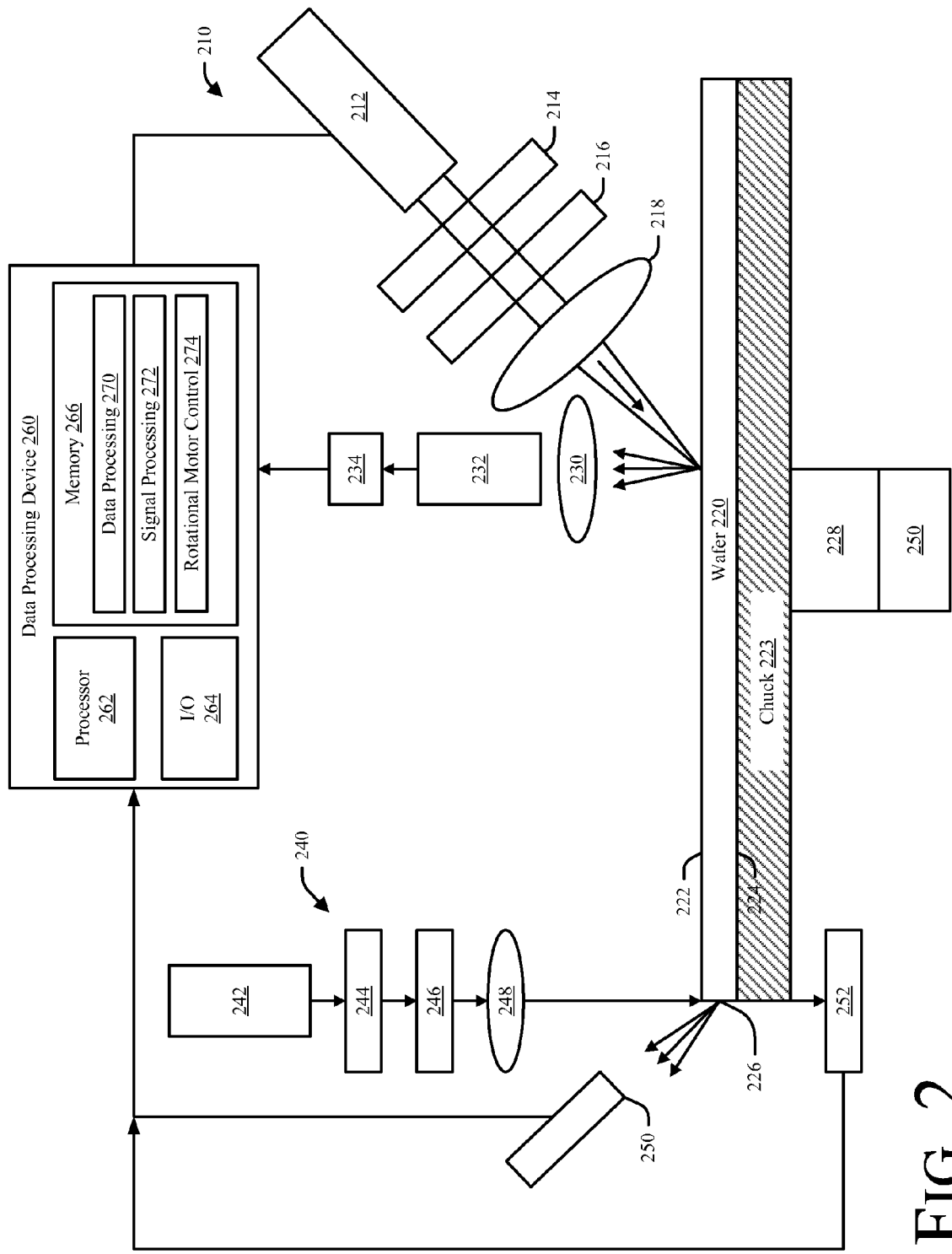
FIG. 2 is a schematic illustration of various components of a surface inspection system, according to embodiments.

FIG. 2 is a schematic illustration of various components of a surface inspection system, according to embodiments. Referring to FIG. 2, in one embodiment, an object such as, e.g., a wafer 220 may be mounted on a chuck 223, which is in turn mounted on a rotatable spindle assembly 228. The spindle assembly 228 and chuck 223 may be rotated by a drive assembly 280 which may include a suitable motor or other drive device. Wafer 220 includes an upper surface 222, a lower surface 224, and an edge surface 226, which may be substantially flat or curved when viewed in a cross-sectional profile. In the embodiment depicted in FIG. 2, the wafer edge surface is flat when viewed in cross-sectional profile.

A first radiation targeting assembly 210 is positioned to direct radiation onto a surface of wafer 220. In the embodiment depicted in FIG. 2, surface analyzer assembly 210 includes a laser diode 212, an optional polarizer 214, an optional half-wave plate 216, and a focusing lens 218 for directing radiation onto a surface of wafer 220. These components target radiation from the laser diode onto the surface of wafer 220, and hence may be considered a radiation targeting assembly. In alternative embodiment polarizer 214 and half-wave plate 216 may be omitted.

Surface analyzer assembly 110 further includes a collecting lens 230 and a photomultiplier tube (PMT) 232. These components collect radiation scattered by the surface of the wafer 120, and hence may be considered a scattered radiation collecting assembly. In alternative embodiments the PMT 232 and collecting lens 230 may be replaced with an integrating sphere or an ellipsoidal mirror together with a PIN photodiode or avalanche photodiode.

At least a portion of the radiation collected by the radiation collected assembly is input to a detector 234, which generates a signal from the scattered radiation. In one embodiment, detector 134 may be a PIN photodetector available from Hamamatsu, Inc.

In one embodiment surface analyzer assembly 210 uses a multi-mode, multi-wavelength laser diode 212 which is available from Rohm Co., LTD Kyoto, Japan as model number RLD-78MV and a polarizer 214 which is adjusted for P polarization and improves the extinction ratio of the laser. The radiation may be of any wavelength. In one embodiment a 405 nm violet source available from Coherent, Inc may be implemented. In another embodiment a 635 nm source may be implemented. The mechanically rotatable half wave plate 216 is available from CVI Laser Corp. and can be used to rotate the polarization between 45 degrees, and P or S polarization's. Alternative techniques for rotating the polarization include rotating the laser diode 212 or to use a liquid crystal polarization rotator such as model LPR-100 available from Meadowlark Optics, Frederick, Colo. The latter embodiment has the advantage of being a purely electronic means of polarization rotation and as a result there is no possibility of beam movement when the polarization is rotated.

Focusing lens 218 creates a small spot on the surface of a wafer 220. The collecting lens 230, PMT 232, and detector 234 and are used to generate a signal from the scattered radiation for the purposes of computing the surface roughness, measuring debris, detecting stains, cracks, scratches, delaminations, blisters or corrosion on the disk or wafer 220 surface or edge 226 or near edge regions.

A second radiation targeting assembly 240 is positioned to direct radiation onto the edge of wafer 220. In the embodiment depicted in FIG. 2, second radiation targeting assembly 240 includes a laser diode 242, an optional polarizer 244, an optional half-wave plate 246, and a focusing lens 248 for directing radiation onto the edge of wafer 220. These components may be embodied as described above with reference to the first radiation targeting assembly 210. These components target radiation from the laser diode onto the surface of wafer 220, and hence may be considered a radiation targeting assembly. In alternative embodiment polarizer 214 and half-wave plate 216 may be omitted.

In some embodiments laser diode 242 operates at a wavelength different from the wavelength at which laser diode 212 operates. Similarly, in some embodiments a single laser diode may be used, and the beam emitted from the laser diode may be split, e.g., using a beam splitter or partial mirror into a first beam which may be directed onto the surface 222 of wafer 220 and a second beam which may be directed onto the edge 226 of wafer 220.

In the embodiment depicted in FIG. 2, radiation from the radiation targeting assembly 240 is incident on the edge surface in a direction substantially parallel to the surface. In alternate embodiments, radiation from the second radiation directing assembly 240 may be directed onto the edge surface at different incidence angles, e.g., from zero degrees to about five degrees.

A portion of the radiation from the second radiation targeting assembly 240 will be scattered from the edge surface 226 of wafer 220. A portion of the scattered radiation will be incident on detector 250, which generates a signal set from the scattered radiation. Another portion of the radiation from the second radiation targeting assembly 240 passes by the edge surface 226 and is incident on detector 252, which generates a signal set based on the radiation incident on the detector 250. Detector 252 may be referred to as a throughbeam detector. In one embodiment, detectors 250, 252 may be embodied as PIN photodetectors available from Hamamatsu, Inc.

In one embodiment, the system comprises a data processing device 260 which in turn comprises a processor 262 one or more input/output ports 264 and a memory module 266. Memory module 266 includes a computer readable medium such as, for example, random access memory (RAM), magnetic memory such as a hard disk drive, read only memory (ROM) or the like. The computer readable medium in turn comprises logic instructions which define a data processing module 270, a signal processing module 272, and a rotational motor control 174.

Data collected by the collectors 234, 250, 252 is input via the I/O ports 264 to the data processing device 260. The data processing device 260 implements logic instructions that enable the instrument described in FIG. 2 to measure one or more characteristics of the surfaces 220, 226, and to locate the edge of wafer 220.

Figure 3:
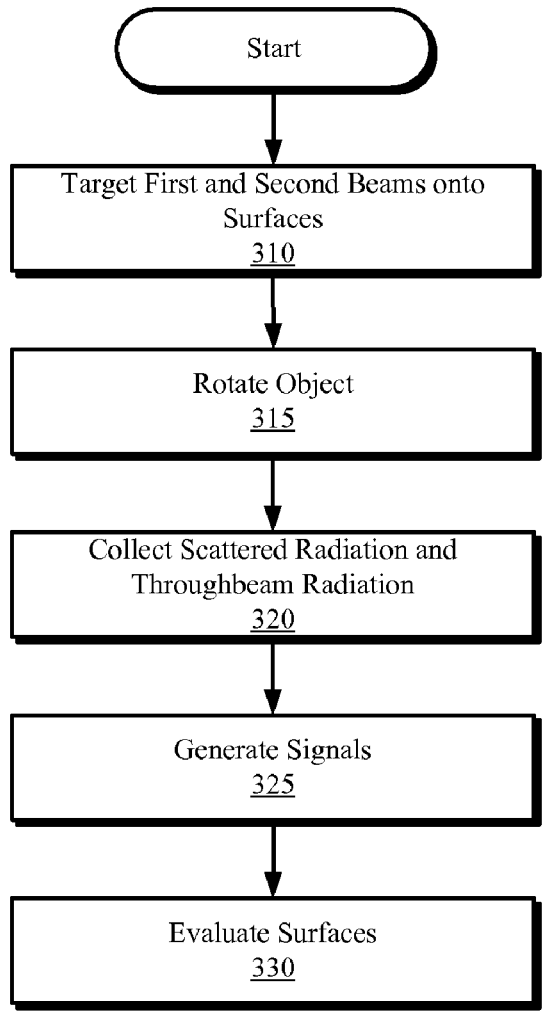
FIG. 3 is a flowchart illustrating operations in an embodiment of a method for contemporaneous surface and edge inspection, according to embodiments.

FIG. 3 is a flowchart illustrating operations in an embodiment of a method for contemporaneous surface and edge inspection, according to embodiments. Referring to FIG. 3, at operation 310 first and second beams are targeted onto the surfaces of the object being scanned. For example the first and second beams may correspond to the beams originating from the first radiation targeting assembly and the second radiation targeting assembly, as described above.

At operation 315 the object is rotated about a central axis. For example, the object may be positioned on a rotating spindle as described above, which is rotated about a central axis by drive assembly 280. At operation 320 radiation from the primary and secondary beams that is scattered from the surface of the object is collected by the respective radiation collection assemblies, and at operation 325 the respective detectors generate signal sets from the reflected radiation.

At operation 330 one or more characteristics of the surfaces are evaluated. Characteristics of surfaces 220, 226 may be determined using one or more of the techniques described in U.S. Pat. Nos. 6,538,730, 6,271,916, 6,201,601, 6,956,660, 7,218,391, and 7,061,601, the disclosures of which are incorporated herein by reference in their entirety.

Figure 4:
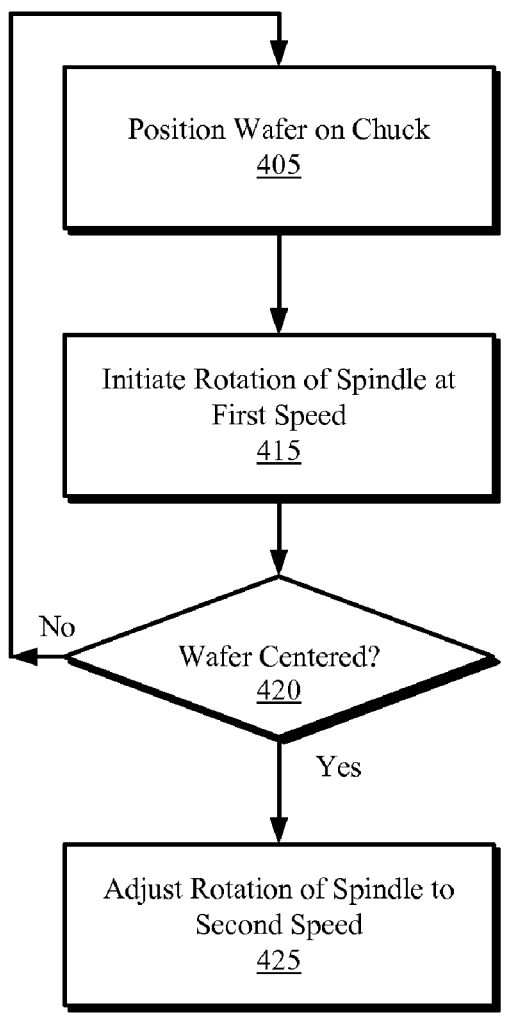
FIG. 4 is a flowchart illustrating operations in an embodiment of a method including multispeed rotation, according to embodiments.

In some embodiments, the system includes a rotational motor control module 274 which uses edge location data from the detector 252 to implement a multi-speed rotation process for rotating the spindle on which the wafer is mounted. In one embodiment as depicted in FIG. 4, a wafer is positioned on the chuck (operation 405) mounted on the spindle, which is then rotated (operation 415) at a first, relatively low speed. Data from the detector 252 is used to determine the edge location of the wafer. From this data the location of the central axis the wafer may be determined.

If, at operation 420, the wafer is properly centered on the spindle, i.e., if the central axis of the wafer coincides with the central axis of the spindle, then control passes to operation 425 and the rotational speed of the rotation of the spindle is adjusted to a second speed, which may be higher than the first speed. By contrast, if at operation 420 the wafer is not properly centered then control passes back to operation 405 and the wafer may be repositioned on the chuck.

Thus, described herein are systems and methods which utilize a first beam and a second beam to implement contemporaneous wafer surface and edge inspection. In some embodiments the radiation beams may be from different sources, which permits the respective parameters, i.e., wavelength, power, spot size, etc., of the lasers to be selected independently, which in turn enhances the ability of the system to detect defects.

Some of the methods described herein may be embodied as logic instructions on a computer-readable medium. When executed on a processor, the logic instructions cause a processor to be programmed as a special-purpose machine that implements the described methods. The processor, when configured by the logic instructions to execute the methods described herein, constitutes structure for performing the described methods. Alternatively, the methods described herein may be reduced to logic on, e.g., a field programmable gate array (FPGA), an application specific integrated circuit (ASIC) or the like.

Reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A system to analyze a surface of a substrate, comprising:
a chuck for receiving the substrate,
a motor for rotating the chuck around a central axis of the chuck at a rotational speed,
a surface inspection assembly having,
   a first targeting assembly to direct a first light beam onto the surface of the substrate, the first light beam reflecting from the surface and thereby creating a first scattered light beam,
   a first collecting assembly to collect at least some of the first scattered light beam, and
   a first detector assembly coupled to the first collecting assembly to generate a first signal from the first scattered light beam,
an edge detection assembly having,
   a second targeting assembly to direct a second light beam across an edge of the substrate, the edge of the substrate passing a portion of the second light beam, and reflecting a portion of the second light beam and thereby creating a second scattered light beam, where the second light beam is directed contemporaneously with the first light beam, and
   a throughbeam detector to collect the passed portion of the second light beam and to generate a third signal from the passed portion of the second light beam, wherein the third signal indicates a degree of alignment between a center of the substrate and the central axis of the chuck as it rotates, and
a data processing module to receive the first signal and the third signal and to analyze the surface of the substrate using the first signal when the third signal indicates a sufficient degree of alignment between the rotating substrate and chuck
wherein a single light source creates both the first light beam and the second light beam, and the first light beam and the second light beam have different wavelengths to each other.

2. The system of claim 1, wherein the edge detection assembly is physically displaced from the surface inspection assembly.

3. The system of claim 1, wherein the edge detection assembly directs light onto the edge of the substrate at an incidence angle that varies from normal by between about zero degrees and above five degrees.

4. The system of claim 1, further comprising an edge inspection assembly having:
- a second collecting assembly to collect portions of the second scattered light beam, and
- a second detector assembly coupled to the second collecting assembly to generate a second signal from the second scattered light beam.

5. The system of claim 4, wherein the data processing module further comprises a rotational speed control module to use the second signal to regulate the rotational speed.

6. The system of claim 1, further comprising a drive assembly to impart linear motion between the surface inspection assembly and the substrate.

7. A method to analyze a surface of a substrate, comprising:
- receiving the substrate with a chuck,
- rotating the chuck with a motor around a central axis of the chuck at a rotational speed,
- directing a first light beam onto the surface of the substrate, the first light beam reflecting from the surface and thereby creating a first scattered light beam,
- collecting at least some of the first scattered light beam,
- generating a first signal from the first scattered light beam,
- directing a second light beam across an edge of the substrate, the edge of the substrate passing a portion of the second light beam, and reflecting a portion of the second light beam and thereby creating a second scattered light beam, where the second light beam is directed contemporaneously with the first light beam,
- collecting the passed portion of the second light beam,
- generating a third signal from the passed portion of the second light beam, wherein the third signal indicates a degree of alignment between a center of the substrate and the central axis of the chuck as it rotates, and
- analyzing the surface of the substrate using the first signal when the third signal indicates a sufficient degree of alignment between the rotating substrate and chuck
- wherein a single light source creates both the first light beam and the second light beam, and the first light beam and the second light beam have different wavelengths to each other.

8. The method of claim 7, wherein the second light beam is directed onto the edge of the substrate at an incidence angle that varies from normal by between about zero degrees and above five degrees.

9. The method of claim 7, further comprising:
- collecting portions of the second scattered light beam,
- generating a second signal from the second scattered light beam, and
- using the second signal to regulate the rotational speed.

* * * * *